(12) United States Patent
Chiu et al.

(10) Patent No.: US 8,022,243 B1
(45) Date of Patent: Sep. 20, 2011

(54) LOW ODOUR OLIGOMERIC PHOTOINITIATOR AND METHOD OF MAKING THE SAME

(75) Inventors: Chingfan Chris Chiu, Taipei (TW); Yi-Hsun Yang, Taipei (TW)

(73) Assignee: Chitec Technology Co. Ltd.

( * ) Notice: Subject to any disclaimer, the term of this patent is extended or adjusted under 35 U.S.C. 154(b) by 0 days.

(21) Appl. No.: 12/800,795

(22) Filed: May 24, 2010

(51) Int. Cl.
*C07C 321/00* (2006.01)
*C07C 323/00* (2006.01)
*C07C 381/00* (2006.01)

(52) U.S. Cl. ........................................................ 560/17
(58) Field of Classification Search ........................ None
See application file for complete search history.

(56) References Cited

U.S. PATENT DOCUMENTS

| | | | |
|---|---|---|---|
| 4,582,862 A | 4/1986 | Berner et al. | 522/14 |
| 5,145,885 A | 9/1992 | Berner et al. | 522/39 |
| 6,048,667 A | 4/2000 | Eldin et al. | |
| 6,673,850 B1 * | 1/2004 | Yamato et al. | 522/33 |
| 7,612,122 B2 | 11/2009 | Herlihy et al. | |
| 2004/0068110 A1 | 4/2004 | Chiu et al. | 265/30 |

OTHER PUBLICATIONS

Demina et al., Russian Journal of Organic Chemistry, 2002, 38(12), 1810-1811.*
Padias, A. Buyle; Journal of Polymer Science, Polymer Chemistry, 1981, 19(4), p. 1021-1032.

* cited by examiner

*Primary Examiner* — Daniel Sullivan
*Assistant Examiner* — Jennifer C Sawyer

(57) ABSTRACT

Disclosed herein are a class of low odor oligomeric photoinitiators produced from the poly-condensation of dimethyl dicarboxylates and diols of a photo-active moiety. The disclosed oligomeric photoinitiators exhibited comparable photo-curing speed and much lower odor and extractability to its analogue of small molecular weight photoinitiators. Also disclosed are the preparation methods of the photoinitiators, and their applications in photopolymerizable compositions.

6 Claims, 5 Drawing Sheets

Formula (I)   n=2

PA= PA-1    R= R-6

LOW ODOUR OLIGOMERIC PHOTOINITIATOR AND METHOD OF MAKING THE SAME

FIELD OF THE INVENTION

The present invention relates to a new class of low odour oligomeric photoinitiator, and the preparation technologies and uses of the same.

BACKGROUND OF THE INVENTION

A photoinitiator is scientifically a compound transforming the physical energy of light into suitable chemical energy in the form of reactive species. Upon absorption of light with a specific wavelength, it undergoes a photoreaction, producing reactive species, and these reactive species may be free radicals for a free radical polymerization system or cations for a cationic polymerization system.

The photochemical polymerization of unsaturated monomers and pre-polymers is a well known methodology and has wide industrial applications from radiation coating to radiation printing. The most reactive photosensitive systems for radical polymerization reactions are usually the cleavable photoinitiators, and particularly these derived from acetophenone. In these photosensitive systems, the photoinitiators are excited into their singlet state and covert, through intersystem crossing, to their triplet state. These excited states can undergo a direct formation of two radicals. Then, one or both of these radicals can initiate the polymerization reaction through an addition reaction onto the monomer double bond leading to the first monomeric radical.

For example, U.S. Pat. No. 4,582,862 discloses specifically an acetophenone-type photoinitiator, 2-methyl-1-[4-(methylthio)phenyl]-2-morpholino-propane-1-one (MMMP), which has been widely used as a photoinitiator nowadays, under the commercial name of Irgacure 907 from Ciba, Basel. Upon excitation of UV-light, The MMMP molecule undergoes a bond cleavage and generates two free radicals as shown in Scheme-1.

After polymerization and post-curing, these free radicals are quenched and mostly remained in polymeric matrix as low molecular weight residues. In the case of MMMP, these residue molecules include 4-methylthiobenzaldehyde and N-isopropylmorpholine as exampled in Scheme-1. The yielded residue molecules, in particular, the sulphur-containing fragment, 4-methylthiobenzaldehyde, not only generates a strong irritated odour, but also causes respiratory tract irritation if inhaled and skin irritation if absorbed through skin.

In order to reduce the irritation and odour, researchers have investigated many MMMP derivatives without sulphur content, such as these disclosed in U.S. Pat. No. 5,145,885 and U.S. Pat. No. 6,048,667. Even though some of these derivatives, did exhibit less odour than MMMP, when being used as a replacement for MMMP in ink formations, they found limited applications due to their thermal and mechanic un-stability. By incorporating selected stabilizers into the ink formulation may improve the ink stability and improve its shelf-life, but the addition of polymerization stabilizers often retards the photo-curing speed, eventually reduce the photo-initiation efficiency of such photoinitiators.

In view of the limitation of small molecular weight photoinitiators, macro-type photo-initiators have drawn increasingly interest especially for UV-curable formulations. Improvements have been claimed in terms of low-odour and non-yellowing properties.

For instance, Hitoshi Yamato et al in U.S. Pat. No. 6,673,850 assigned to Ciba Specialty Chemicals Corporation disclosed a class of marcophotoinitiators comprising chain transfer groups and these macrophotoinitiators were claimed to be polymerized to yield block copolymers. Shaun Lawrence Herlihy in U.S. Pat. No. 7,612,122 assigned to Sun Chemical Corporation described a group of dendrimer-type marcophotoinitiators with poly-hydroxy as the linking core.

Furthermore, Chingfan Chris Chiu in US Patent Application (US2004/0068110) disclosed a group of polyester-linked marcophotoinitiators. The disclosed polyester-linked marcophotoinitiators increased the length of the sulfur terminal by chemically bonding to a polyester chain, thus offered the advantage of low volatility and low odor after curing. However, like most of polymeric photoinitiators disclosed in the prior art, this group of polyester-linked macrophotoinitiators also suffer from the lower photo-curing speed than the traditional small molecular weight photoinitiators, though they consist of the same cleavable function moiety, morpholinoketone as that in the traditional small molecular weight photoinitiators such as Igacure 907.

It is now the objective of this invention to provide a photoinitiator which posses the comparable photo-curing speed to that of the analogues of small molecular weight photoinitiators but also posses the advantage of low odor/low extractability of these macrophotoinitiators.

It is another objective of this invention to teach the procedure to manufacture the invented photoinitiators.

Yet, it is still another objective of this invention to describe the use of the invented photoinitiators in radiation curing formulations.

SUMMARY OF THE INVENTION

Accordingly, the present invention provides a low odour oligomeric photoinitiator with the Formula (I).

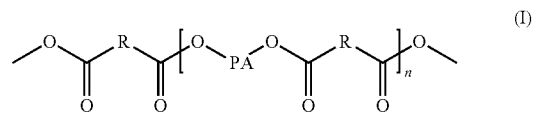

Wherein, PA represents a photo-active moiety, R is a common organic moiety, n is an integer from 1 to 10.

Furthermore, the present invention describes that the invented oligomeric photoinitiator of Formula (I) can be produced by transesterification of a photo-active moiety containing diol of Formula (II) and a dimethyl dicarboxylate of Formula (III).

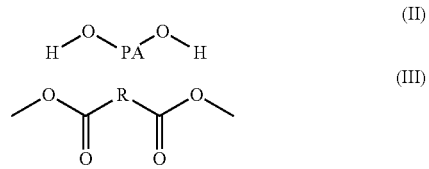

Wherein, PA and R in Formula (II) and (III) respectively are of the same definition as these in Formula (I).

Still furthermore, the present invention encompasses the applications of the compound of formula (I). More specifically, the compound of formula (I) according to the present invention can be formulated with a photopolymerizable monomer compound to form a photopolymerizable composition, such as an UV curable ink.

The above and other objects, features and advantages of the present invention will be apparent with reference to the following detailed description of the preferred examples.

DETAILED DESCRIPTION OF THE INVENTION

The present invention provides a low odour oligomeric photoinitiator with the Formula (I).

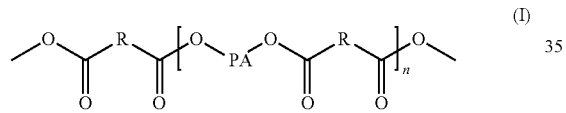
(I)

Wherein, PA represents a photo-active moiety, R is a common organic moiety, n is an integer from 1 to 10.

Furthermore, the present invention describes that the invented oligomeric photoinitiator of Formula (I) can be produced by transesterification (or named poly-condensation) of a diol containing photo-active moiety of Formula (II) and a dimethyl dicarboxylate of Formula (III).

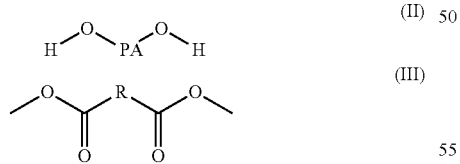
(II)
(III)

Wherein, PA and R in Formula (II) and (III) respectively are of the same definition as these in Formula (I).

As defined in Formula (I) and (II), PA is a photo-active moiety. Preferably, PA is selected from these common small molecular photoinitiators which have exhibited high photo-activity upon UV radiation. Still more preferably, PA is selected from these photoinitiators derived from acetophenone. In particular, the following are two examples of mostly preferable PA according to the present invention.

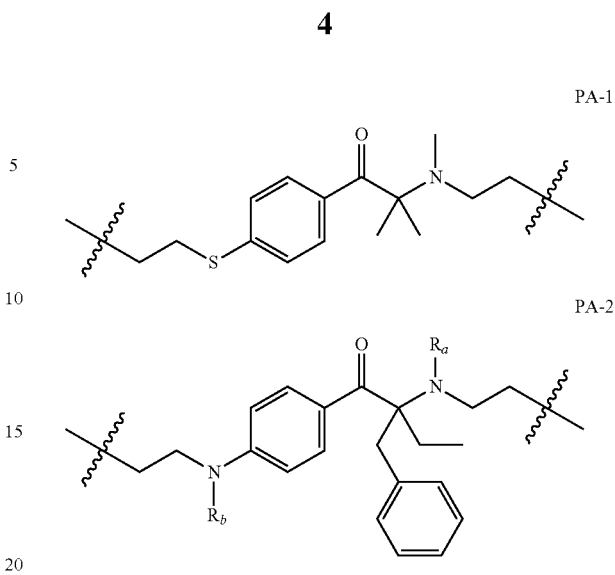

In the listed mostly preferable PA-2, $R_a$ and $R_b$ are preferably selected from a group of alky and substituted alkyl. Still more preferably, $R_a$ and $R_b$ are methyl groups.

As defined in Formula (I) and (III), R represents a common organic moiety. Preferably, R is selected from a group of alkyl, substituted alkyl, phenyl, substituted phenyl, biphenyl, substituted bi-phenyl, pyridine, substituted pyridine. In particular, the following are a few examples of preferable R according to the present invention.

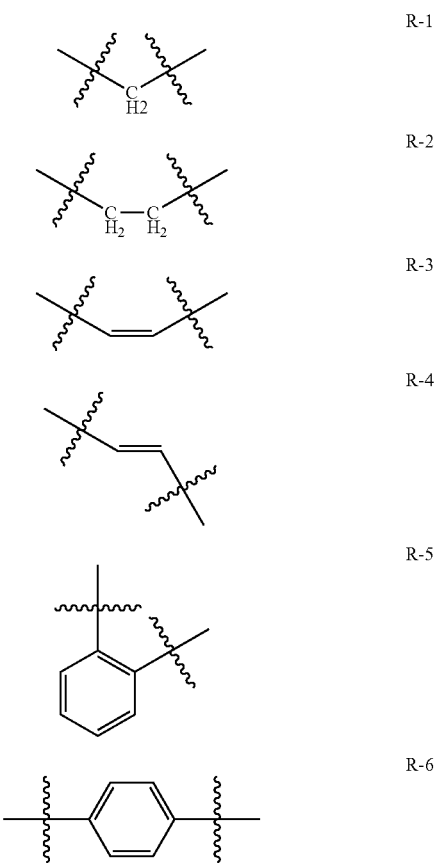

R-7

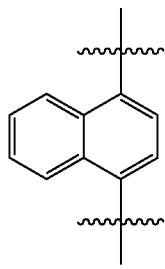

As defined in Formula (I), n is an integral ranging from 1-10. Preferably, n is 1-5, and still more preferably, n is 2-3.

The transesterification of a long chain alcohol with a methyl carboxylate is well-known art. In the present invention, this transesterification is taking place between a diol of Formula-II and a dimethyl dicarboxylate of Formula-III, therefore, the poly-condensation between diol and diester is taking place and a polymeric compound of Formula-I is being generated.

Figure 1:
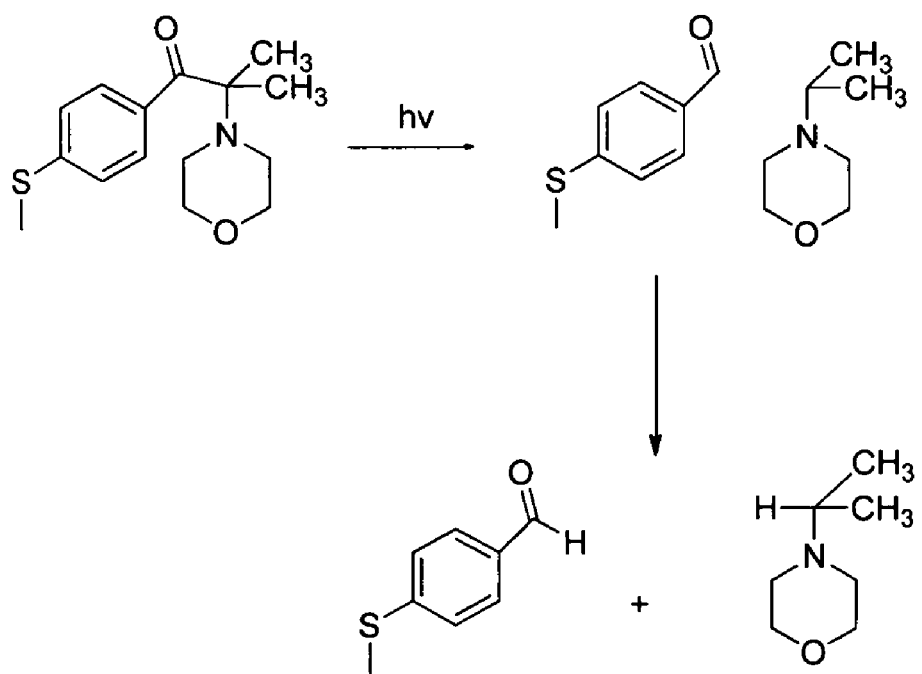
FIG. 1 shows a schematic representation of the generation and the termination of free radicals from the conventional photoinitiator, MMMP.

The terminal group of the poly-condensation product depends on the ratio between two monomers, the monomer of Formula (II) and the monomer of Formula (III). According to the present invention, the molar ratio between the diol (the monomer of Formula (II)) and the dimethyl dicarboxylate (the monomer of Formula (III)) in the poly-condensation shall be less than 1, so that both terminals (or named end-cap) of the polymeric compound are methyl dicarboxylate groups as exhibited in Formula-I. Otherwise, the polymer will be ended with the photo-active containing moiety as expressed in Formula-IV, which is not a preferable structure according to the present invention, because at such a case that the cleavage of the terminal group of PA may result in segments of small molecules of aldehyde residues as it occurs in the case of small molecular photoinitiator, such as MMMP as illustrated in FIG. 1.

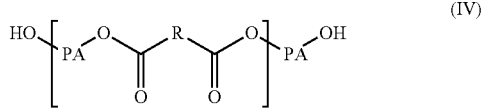
(IV)

It is worth to note that an environmental friendly organic base is used to catalyze this poly-condensation in the present invention. In the prior art, such as described in the reference of Journal of Polymer Science, Polymer Chemistry Edition (1981), 19(4), 1021, tin and other organic transition metallic compounds are often employed for poly-condensation of a diol and a dimethyl dicarboxylate, and these organic transition metallic compounds, in particular these organic-tins, are extremely toxic and harmful to environment. In the present invention, a mild organic base, sodium methoxide is used. Upon the completion of the poly-condensation, it transforms into methanol and sodium hydroxide solution after hydrolysis by water. Therefore, the use of sodium methoxide preferably in the present invention is a green chemistry comparing the processing described in the prior art.

Figure 2:
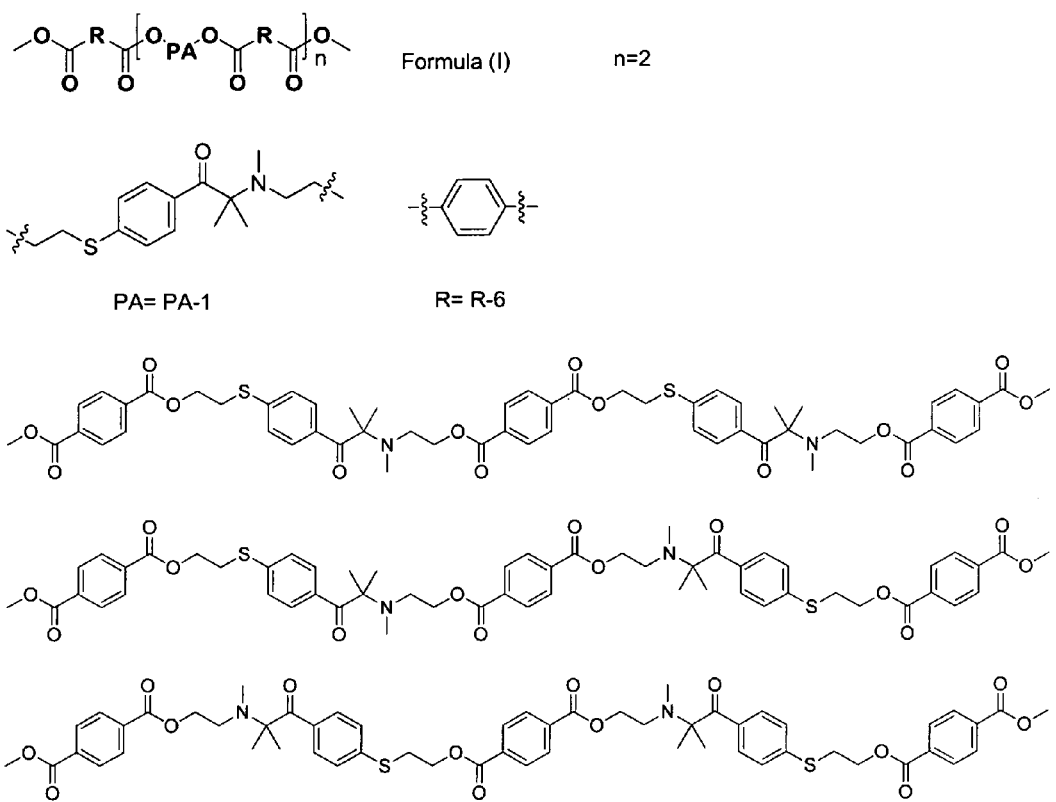
FIG. 2 presents the isomeric configurations of the poly-condensation product from the selected diol and dimethyl carboxylate according to the present invention.

It is still worth to note that there will be many configuration isomers existing in the final polymeric product when an asymmetric diol containing the photo-active moiety or an asymmetric dimethyl dicarboxylate is employed to produce Formula (I) by poly-condensation. For example, when R=R-6 and PA=PA-1 as listed above, for n=1, the Formula (I) may include these configuration isomer as exampled in FIG. 2. For n=2 or greater, there exit more configuration isomers. Therefore, the final product shall be viewed as a random mixture of these isomers.

Furthermore, the present invention envisions the applications of the compound of formula (I). According to the present invention, the compound of formula (I) is useful as a photoinitiator, and it neither has the odour problem usually associated with MMMP nor undesirably retard the photo-curing speed usually associated with the polymeric photoinitiators. Therefore, according to the available methodologies that are well known in the art, the compound of formula (I) according to the present invention can be formulated with a photopolymerizable monomer, a photosensitizer, a pigment or a dyestuff, and other additives commonly employed by those skilled in the art in the preparation of a photopolymerizable composition, such as oligomers, photosensitizers, amine synergists and other physical property modifiers.

It is contemplated that the compound of formula (I) according to the present invention can be used in different industries, e.g. those involving the use of a photoinitiator as mentioned in the prior art references cited above. For example, the compound of formula (I) according to the present invention can be formulated in UV inks or coatings to act as a photoinitiator. It is also contemplated that the compound of formula (I) according to this invention can be used in combination with the conventional photoinitiators, such as those photoinitiators disclosed in the prior art references cited above, especially the ones disclosed in U.S. Pat. No. 4,672,079.

EXAMPLES

The invention will now be described in more detail with reference to the following examples. However, it should be understood that these examples are given for the purpose of illustration only and are not intended to limit the scope of the present invention.

Figure 3:
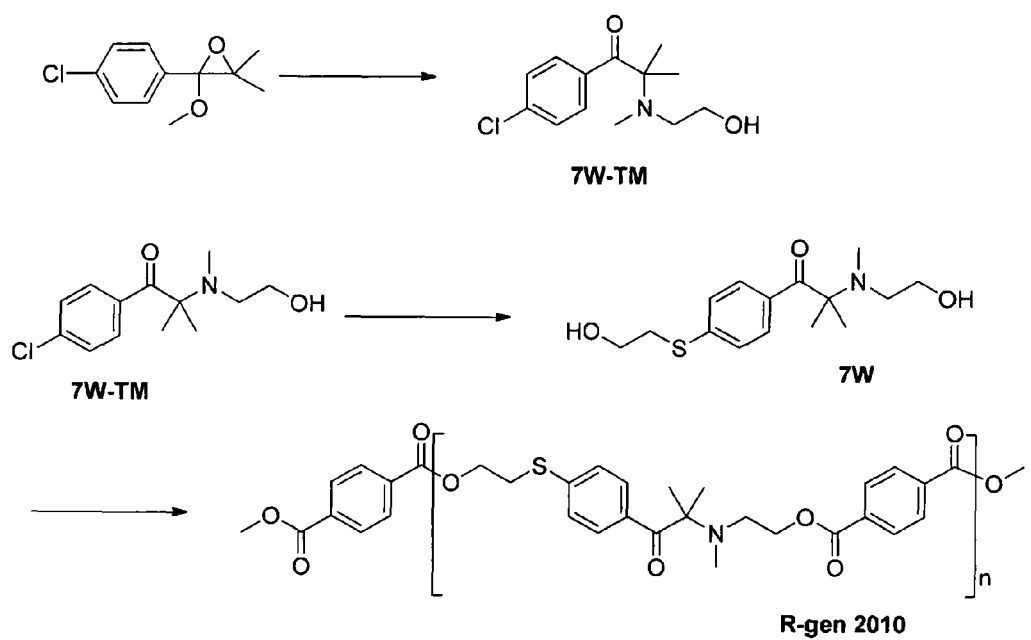
FIG. 3 schematically presents the synthetic pathway of the invented polymeric photoinitiator R-gen 2010.

In the following examples, common chemicals and reagents are purchased from the commercial sources as specified in the text, and compounds not available commercially are synthesized in Chitec Technology Corporation, and will be described in the examples of this invention. FIG. 3 schematically presents the synthetic pathway of the invented polymeric photoinitiator R-gen 2010. Not only the oligomeric structure of R-gen-2010 is first-time disclosed in the present invention, but also the intermediate 7W-TM and the oligomeric precursor 7W used to prepare the invented R-gen-2010 are new compounds which have not been disclosed in any prior art. The detailed procedures for the preparation of this oligomeric compound and its precursor 7W are now given in the following examples.

Example 1

Synthesis 7W-TM

Into a three neck reaction flask, 212 g (1 mol) of 2-(4-chlorophenyl)-2-methoxy-3,3-dimethyloxirane and 225 g (3 mol) of 2-(methylamino) ethanol were admitted, and then 13.1 g (0.05 mol) of triphenylphosphene were added to the mixture. The resulted mixture was stirred for 7 hrs at 110° C. After the reaction completed, the excess of 2-(methylamino) ethanol was then distilled off. After the resulted residue was cooled to 60° C., the precipitation was observed upon adding 450 g of water. The precipitated product was filtered and finally dried in a vacuum oven to yield 204 g (0.8 mol, 80%) of 1-(4-chlorophenyl)-2-((2-hydroxyl)(methyl) amino)-2- methylpropan-1-one, named the product of 7W-TM with a melting point of 70-73° C. $^1$H NMR (CDCl$_3$): δ=7.57 (d, 2H, J=8.4), 7.30 (d, 2H, J=8.7), 4.26 (td, 1H, J$_t$=12.3, J$_d$=4.3), 3.75 (dd, 1H, J$_1$=11.7, J$_2$=4.5), 2.93 (td, 1H, J$_t$=12.5, J$_d$=4.8), 2.381 (dd, 1H, J$_1$=12, J$_2$=3.9), 2.27 (s, 3H), 0.96 (s, 6H).

Example 2

Synthesis of 7W 25.6 g (0.1 mol) of 7W-TM obtained in Example-1, 9.24 g (0.16 mol) of potassium hydroxide and 23.4 g (0.3 mol) of 2-mercaptoethanol were dissolved in 180 g (2 mol) of N,N-dimethyl acetamide. The mixture was stirred at 80° C. for 6 hrs. The excesses of 2-mercaptoethanol and N,N-dimethyl acetamide were distilled off at 80° C. After the reaction mixture was allowed to cool down to 60° C., 100 g of water was added, and then the resulted mixture was stirred at room temperature for 3 hrs. Consequently, the crude product was precipitated and collected by filtration. The obtained crude product was further purified by re-crystallized in 75 g of toluene to yield (23.7 g, 80%) 2-((2-hydroxyethyl)(methyl) amino)-1-(4-((2-hydroxyethyl)thio) phenyl)-2-methylpropan-1-one, named the product of 7W with a melting point of 106-114° C. $^1$H NMR (CDCl$_3$): δ=7.52 (d, 2H, J=6.45), 7.31 (d, 2H, J=6.45), 4.24 (td, 1H, J$_t$=12.6, J$_d$=4.2), 3.71 (m, 3H), 3.10 (t, 2H, J=6), 2.91 (td, J$_t$=12.6, J$_d$=4.2, 1H), 2.37 (dd, J$_d$=4.2, J$_d$=9, 1H), 2.18, (s, 3H), 0.93 (S, 6H)

Example 3

Synthesis of 8W

The compound 8W(2-benzyl-2-((2-hydroxyethyl)(methyl)amino)-1-(4-((2-hydroxyethyl) (methyl) amino) phenyl) butan-1-one was prepared in a similar method to that used in the preparation of 7W (2-((2-hydroxyethyl)(methyl)amino)-1-(4-((2-hydroxyethyl)(methyl) amino) phenyl)-2-methyl-propan-1-one) as described in Example 1. Specifically, 286 g (1 mol) of 2-benzyl-2-ethyl-3-(4-fluorophenyl)-3-methoxyoxirane and 375 g (5 mol) of 2-(methylamino) ethanol were admitted into a three neck reaction flask, and then 13.1 g (0.05 mol) of triphenylphosphene were added to the mixture. The resulted mixture was stirred for 15 hrs at 120° C. After the reaction completed, the excess of 2-(methylamino) ethanol was then distilled off. After the resulted residue was dissolved in Toluene and washed with water. The organic layer was then evaporated and resulting 268 g (0.7 mol, 70%) of brown sticky liquid, 2-benzyl-2-((2-hydroxyethyl)(methyl)amino)-1-(4-((2-hydroxyethyl)(methyl)amino)phenyl)butan-1-one, named the product of 8W. $^1$H NMR (CDCl$_3$): δ=8.25 (2H), 7.20 (5H), 6.68 (2H), 3.78 (2H), 3.51 (4H), 3.22 (2H), 3.04 (3H), 2.70 (2H), 2.23 (3H), 2.17 (2H), 0.73 (3H).

Example 4

Synthesis of R-gen 2010

To synthesize compound of formula (I) wherein R=R-6 and PA=PA-1, 44.6 g (150 mmol) of 7W obtained in Example-2, 34.92 g (180 mmol) dimethyl terephthalate and 405 mg of sodium methoxide were dissolved in 600 mL of Toluene. The resulted solution was heated to reflux, and water was continuously removed with Dean-Stark during this reflux period. The poly-condensation was monitored with a GPC (Gel Permeation Chromatography) system, and stopped when a desired molecular weight was reached as evidenced from GPC profile. Celite powder was added into the reaction system, and all the solid phase was then filtrated off. The liquid phase was then concentrated with a rotary evaporator to yield 75 g of sticky wine-color solid, named the product of R-gen 2010.

Other compounds of formula (I), for examples where in R=R-2, R-3, R-4 and PA=PA-1, were prepared in analogous of R-gen 2010. The resulting products from these exampled variations are in the form of yellow to orange sticky solid.

Example 5

Characterization of R-gen 2010

Figure 4:
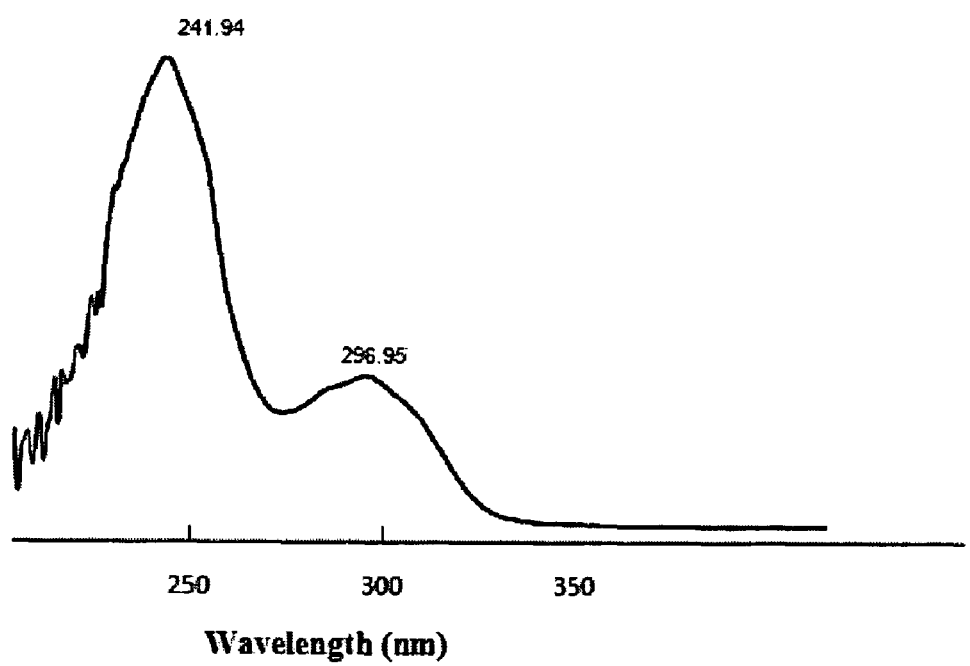
FIG. 4 presents the absorption spectrum of the invented polymeric photoinitiator R-gen 2010.

FIG. 4 presents the absorption spectrum of the R-gen 2010. One major peak at 300 nm is attributed to π to π* absorption band of the acetophenone which is the cleavable function group when excited at an UV radiation. Another major peak at 243 nm is attributed to the linking group, which is not cleavable under the condition of UV radiation for photo-polymerization. This spectrum also exhibits that the absorption wavelength of the invented oligomeric photoinitiator is closed to that of its small molecular weight analogues (for example Igacure 907), which may imply that its photo-curing speed may be similar to that of the small molecular weight analogues.

Figure 5:
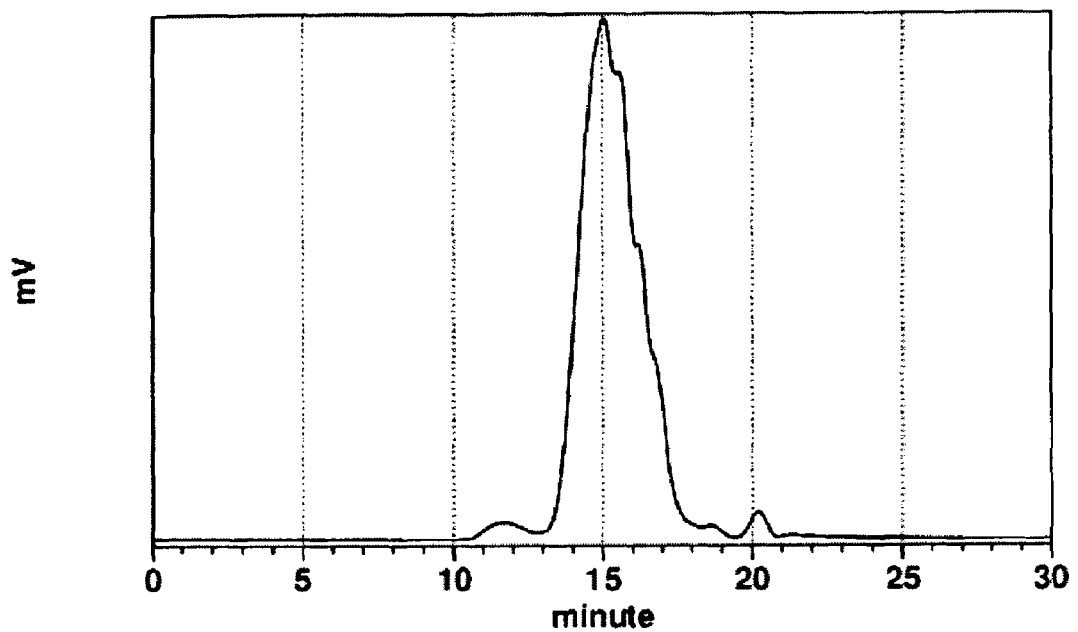
FIG. 5 illustrates the GPC profile of the invented polymeric photoinitiator R-gen 2010.

GPC (Gel Permeation Chromatography) is a standard method to measure the molecular weight of a polymer. The GPC profile of the invented oligomeric photoinitiator R-gen 2010 is presented in FIG. 5. For this particular batch, $M_n$ of 908 and $M_w$ of 1577 are observed, which gives a $M_w/M_n$ ratio (also called PD) of 1.74.

Table-1 summarizes the typical properties of the invented polymeric photoinitiator R-gen 2010.

TABLE 1

| Physical Properties of R-gen 2010 | |
|---|---|
| Item | Description |
| Appearance | Sticky solid |
| Molecular weight ($M_W$) | ~1500 |
| Density | 1.118 g/cm$^3$ @ 20° C. |
| Absorption wavelength | 300 nm |

Example 6

UV Ink Base (Vehicle)

Three UV ink bases (vehicles) were prepared with these ingredients as listed in Table 2. Parts and ratios in weight were used throughout the text unless otherwise specified.

TABLE 2

Typical UV curable ink vehicles

| Ingredient | Red Base | Yellow Base | Blue Base |
|---|---|---|---|
| (1) Polyester tetra-acrylate | 12 | 12 | 12 |
| (2) Aromatic Urethane Hexa-acrylate | 9 | 9 | 9 |
| (3) Bisphenol-A Epoxy Diacrylate | 8 | 8 | 8 |
| (4) Propoxylated Glycerol Triacrylate | 15 | 15 | 15 |
| (5) Diluted Chlorinated Polyester | 30 | 30 | 30 |
| (6) Pigment Rubine F6B | 20 | | |
| (7) Pigment Fast Yellow 4181G | | 20 | |
| (8) Pigment blue | | | 20 |

(1) Polyester Tetra-Acrylate: EB 657, from Cytec
(2) Aromatic Urethane Hexa-Acrylate: EB 220, from Cytec
(3) Bisphenol-A Epoxy Diacrylate: EB 600, from Cytec
(4) Propoxylated Glycerol Triacrylate : OTA 480, from Cytec
(5) Diluted Chlorinated Polyester: Eb 436, from Cytec
(6) Red pigment: Clariant Permanent Rubine F6B, CI. No. 12487
(7) Yellow pigment: DAINIPPON INK & Chemicals Incorporated Symuler Fast Yellow 4181G (C.I.Y-83)
(8) Blue pigment: DAINIPPON INK & Chemicals Incorporated, Fastogen Blue TGR (C.I. Pigment Blue 15:3)

Example 7

UV Ink Formulations

Different photoinitiators were then added into the UV ink bases prepared in Example 6 (Table-2) to have the UV-ink formulations as listed in Table-3.

TABLE 3

Examples of UV ink formulations prepared and evaluated

| Component | Ink 1 | Ink 2 | Ink 3 | Ink 4 | Ink 5 | Ink 6 |
|---|---|---|---|---|---|---|
| Red-base | 100 | 100 | | | | |
| Yellow-base | | | 100 | 100 | | |
| Blue base | | | | | 100 | 100 |
| ITX | 0.6 | 0.6 | 0.6 | 0.6 | 0.6 | 0.6 |
| EPD | 1.2 | 1.2 | 1.2 | 1.2 | 1.2 | 1.2 |
| Irgacure-907 | 4 | — | 4 | — | 4 | — |
| R-gen 2010 | — | 6.4 | — | 6.4 | — | 6.4 |

In these exampled formulations listed in Table-3, ITX represents 2-Isopropylthioxanthone, a common co-photoinitiator commercially available from Chitec Technology Corp. EPD represents Ethyl p-dimethylaminobenzoate, another common co-photoinitiator commercially available from Chitec Technology Corp.

Of these exampled formulations, Ink-1 and Ink-2 are red inks formulated from the red-base prepare in Example-6, and Ink-3 and Ink-4 are yellow inks formulated from the yellow base prepared in Example-6. Ink-5 and Ink-6 are blue inks formulated from the blue-base prepared in Example-6. Ink-1, Ink-3 and Ink-5 are the control formulations made of the conventional photoinitiator Irgacure-907; Ink-2, Ink-4 and Ink-6 are the investigating formulations made of the invented oligomeric photoinitiator R-gen 2010. For the direct comparison of the photo-activity, the concentration of photoactive centers in each ink was controlled at a same level. In this Example, the photoactive center is the acetophenone group bridged with a nitrogen atom through a quaternary carbon atom, therefore, the nitrogen content shall relatively represent the concentration of the photo-active center of the photoinitiators to be compared in this Example. Since the nitrogen content in R-gen 2010 (N %=2.85%) is estimated to be 77% less than that in Irgacure-907 (N %=5.05%), therefore, 77% of more R-gen 2010 than Irgacure-907 were used to formulate the corresponding inks.

Example 8

Photo-Curing Test

These inks as formulated in Example-7 were coated on polypropylene films at 5 micrometer for all six inks evaluated in this example. The printed films were then subjected to ultraviolet radiation via a Fusion F300S UV system at different curing-speeds. After passing the UV chamber, the film was examined and the photo-speed was thus assessed.

Table-4, Table-5 and Table-6 present the photo-speed of the red inks, the yellow inks and the blue inks prepared in Example-7, respectively.

TABLE 4

Curing results of the red inks

| UV energy (mJ/cm2) | Ink 1 (red 907) | Ink 2 (red 2010) |
|---|---|---|
| 23.7 | x | x |
| 35.6 | o | o |
| 47.5 | o | o |
| 53.0 | o | o | o: Cured,
x: Not cured

TABLE 5

Curing results of the yellow inks.

| UV energy (mJ/cm2) | Ink 3 (yellow 907) | Ink 4 (yellow 2010) |
|---|---|---|
| 47.5 | x | o |
| 57.5 | x | o |
| 96.5 | o | o |
| 106.0 | o | o | o: Cured,
x: Not cured

TABLE 6

Curing results of the blue inks.

| UV energy (mJ/cm2) | Ink 5 (blue 907) | Ink 6 (blue 2010) |
|---|---|---|
| 57.5 | x | x |
| 82.2 | x | o |
| 106.0 | o | o |
| 143.7 | o | o | o: Cured,
x: Not cured

Data presented in Table-4 demonstrate that the invented oligomeric photoinitiator R-gen 2010 exhibited a comparable curing speed as that of Igacure-907 for red inks. Table-5 and Table-6 show that both the yellow inks and the blue inks formulated from the invented oligomeric photoinitiator R-gen 2010 required a lower UV energy to cure than those inks formulated from Igacure-907, which indicates that the invented oligomeric photoinitiator R-gen 2010 posses a higher photo-speed than that of Igacure-907 for these UV-curable inks.

Example 9

Extraction Test

Extractability is a measure of the small molecular weight residues left after the photo-curing, which is defined as the division of the extractable amount between the after and the before photo-curing of a given sample under an identical extraction condition, and the extractability is expressed in percentage throughout this text. A high percentage of extractability implies a high residue content after curing, and which is not desirable in the photo-curing system.

To exam the extractability of different photoinitiators, 5 parts of Irgacure 907 and R-gen 2010 were separately but identically mixed with 95 parts of TMPTA (Trimethylolpropane triacrylate, a photo-curable monomer). The resulted mixtures were coated and cured into films, respectively. Then, 1 gram of the cured film was cut and extracted in 10 gram of absolute ethanol at 20° C. for 14 hrs. The yielded extraction liquid was analyzed by a gas phase chromatography, and the extractability was finally calculated as presented in Table-7

TABLE 7

Extractability Determination

| Film sample | Extractability (%) |
|---|---|
| Film- Igacure 907 | 33.0 |
| Film- R-gen 2010 | 1.4 |

Evidently, the invented oligomeric photoinitiator, R-gen 2010, has a much lower extractability than that of the conventional photoinitiator Igacure-907, and shall have much lower odour from the curing film.

What is claimed:

1. A compound of the formula (I):

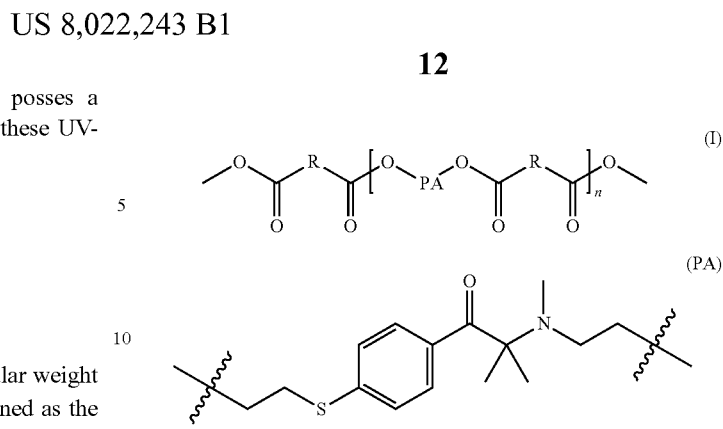

Wherein, PA represents a photo-active moiety of defined structure of PA, R is an aryl group, n is an integer from 1 to 10.

2. A compound of the formula (I) as claimed in claim 1, is produced by transesterification of a photo-active moiety contained diol of Formula (II) and a dimethyl dicarboxylate of Formula (III)

Wherein, PA and R in Formula (II) and (III) respectively are of the same definition as these in Formula (I) of claim 1.

3. A compound as claimed in claim 1, wherein R is a phenyl, and its dimethyl carboxylate form is dimethyl terephthalate.

4. A compound as claimed in claim 1 is a mixture of oligomers and isomers having a general chemical Formula of R-gen 2010

R-gen 2010

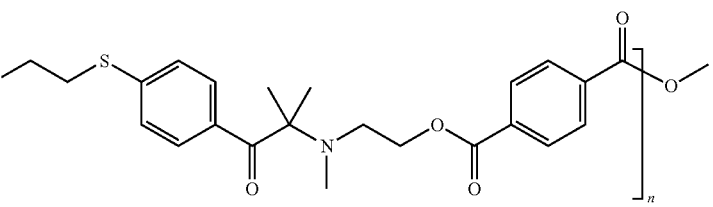

wherein n is integral from 1-10.

5. A photoinitiator comprising a compound as claimed in claim 1.

6. A photopolymerizable composition comprising a compound of formula (I) as claimed in claim 1.

* * * * *